United States Patent [19]

Katz et al.

[11] 4,382,087
[45] May 3, 1983

[54] SELECTED O-(2-TRICHLOROMETHYL-4-PYRIMIDINYL)-O,O-DIALKYL PHOSPHOROTHIONATES AND O-(2-TRICHLOROMETHYL-4-PYRIMIDINYL)-O,O-DIALKYL PHOSPHORONATES AND THEIR USE AS INSECTICIDES

[75] Inventors: Lawrence E. Katz, Orange; Walter A. Gay, Cheshire; Eugene F. Rothgery, North Branford, all of Conn.

[73] Assignee: Olin Corporation, New Haven, Conn.

[21] Appl. No.: 259,791

[22] Filed: May 4, 1981

[51] Int. Cl.³ .................. A01N 57/16; C07F 9/65
[52] U.S. Cl. ........................ 424/200; 544/243
[58] Field of Search ............... 546/243; 424/200

[56] References Cited

U.S. PATENT DOCUMENTS

| | | | |
|---|---|---|---|
| 3,118,889 | 1/1964 | Schroeder | 544/243 X |
| 3,205,231 | 9/1965 | Fest | 544/243 |
| 4,014,882 | 3/1977 | Sharpe | 544/243 |
| 4,168,304 | 9/1979 | Maurer et al. | 424/200 |
| 4,308,258 | 12/1981 | Okabe et al. | 424/200 |

OTHER PUBLICATIONS

Beck et al., Chemical Abstracts, vol. 76, 140857d, (1972).

*Primary Examiner*—Donald G. Daus
*Assistant Examiner*—Diana G. Rivers
*Attorney, Agent, or Firm*—William A. Simons; Thomas P. O'Day

[57] ABSTRACT

Disclosed are selected O-(2-trichloromethyl-4-pyrimidinyl)-O,O-dialkyl phosphorothionates and O-(2-trichloromethyl-4-pyrimidinyl)-O,O-dialkyl phosphoronates having the formula:

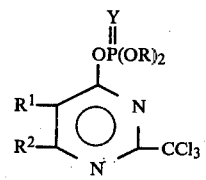

wherein Y is an atom selected from the group consisting of sulfur and oxygen; R is a lower alkyl group having 1 to 4 carbon atoms; $R^1$ is hydrogen, a lower alkyl group having 1 to 4 carbon atoms, halo or nitro; and $R^2$ is a lower alkyl group having 1 to 4 carbon atoms or an amino group. These compounds have been found to exhibit insecticidal activity.

20 Claims, No Drawings

SELECTED O-(2-TRICHLOROMETHYL-4-PYRIMIDINYL)-O,O-DIALKYL PHOSPHOROTHIONATES AND O-(2-TRICHLOROMETHYL-4-PYRIMIDINYL)-O,O-DIALKYL PHOSPHORONATES AND THEIR USE AS INSECTICIDES

BACKGROUND OF THE INVENTION

1. Field of the Invention

This invention relates to selected O-(2-trichloromethyl-4-pyrimidinyl)-O,O-dialkyl phosphorothionates and O-(2-trichloromethyl-4-pyrimidinyl)-O,O-dialkyl phosphoronates and their use as insecticides.

2. Description of the Prior Art

Various substituted O-(4-pyrimidinyl)-O,O-dialkyl phosphorothionates and O-(4-pyrimidinyl)-O,O-dialkyl phosphornates are known to possess different types of pesticidal activity. See, for example, German Pat. No. 3,003,337; U.S. Pat. No. 2,754,243; and U.S. Pat. No. 3,287,453.

BRIEF SUMMARY OF THE INVENTION

Accordingly, the present invention is directed to, as compositions of matter, selected O-(2-trichloromethyl-4-pyrimidinyl)-O,O-dialkyl phosphorothionates and O-(2-trichloromethyl-4-pyrimidinyl)-O,O-dialkyl phosphoronates having the formula:

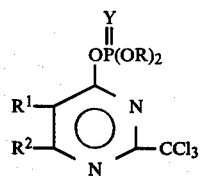

(I)

wherein Y is an atom selected from the group consisting of sulfur and oxygen; R is a lower alkyl group having 1 to 4 carbon atoms; $R^1$ is hydrogen, a lower alkyl group having 1 to 4 carbon atoms, halo or nitro; and $R^2$ is a lower alkyl group having 1 to 4 carbon atoms or an amino group. The present invention is also directed to the use of these compounds as insecticides.

DETAILED DESCRIPTION

The O-(2-trichloromethyl-4-pyrimidinyl)-O,O-dialkyl phosphorothionates and O-(2-trichloromethyl-4-pyrimidinyl)-O,O-dialkyl phosphoronates of the present invention may be prepared by reacting trichloroacetamidine with the corresponding acetoacetate or cyanoacetate, to form the corresponding 4-hydroxy-2-trichloromethylpyrimidine, which is then reacted with a selected dialkyl chlorothiophosphate or dialkyl chlorophosphate. These general reactions are illustrated below in equations (A), (B), (C) and (D). In equation (A), trichloroacetamidine is reacted with methyl acetoacetate to form 4-hydroxy-6-methyl-2-trichloromethylpyrimidine. In equation (B), the 4-hydroxy-6-methyl-2-trichloromethylpyrimidine is reacted with diethyl chlorothiophosphate to form O-(6-methyl-2-trichloromethyl-4-pyrimidinyl)-O,O-diethyl phosphorothionate. In equation (C), trichloroacetamidine is reacted with ethyl cyanoacetate to form 6-amino-4-hydroxy-2-trichloromethylpyrimidine. In equation (D), the 6-amino-4-hydroxy-2-trichloromethylpyrimidine is reacted with diethyl chlorothiophosphate to form O-(6-amino-2-trichloromethyl-4-pyrimidinyl)-O,O-diethyl phosphorothionate.

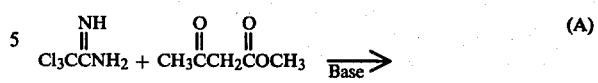

(A)

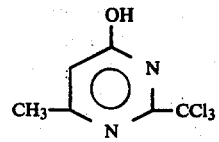

(B)

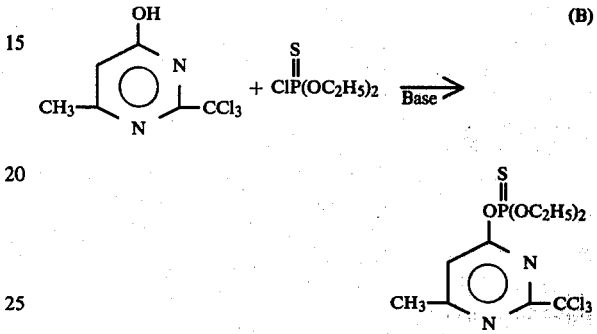

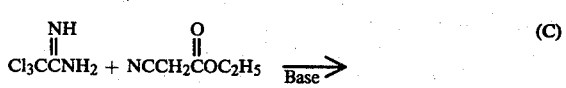

(C)

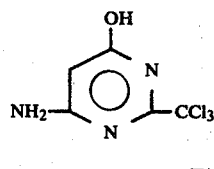

(D)

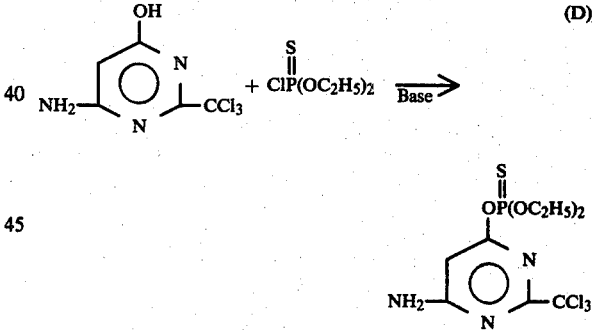

The trichloroacetamidine reactant is made by reacting trichloroacetonitrile with ammonia. Trichloroacetonitrile is a commercially available material. See German Pat. No. 671,785.

The acetoacetate ester reactants may be made by reacting the corresponding acetate with a suitable condensing agent such as sodium ethoxide. See Hickenbottom, W. J., Reactions of Organic Compounds (3rd Edition), pages 359 and 360 (1957). For example, ethyl acetate may be treated with sodium ethoxide, and the resulting mixture acidified to form ethyl acetoacetate. Various acetoacetates such as methyl acetoacetate and ethyl acetoacetate are commercially available.

Illustrative acetoacetate reactants for the compounds of the present invention include the following:
methyl acetoacetate
ethyl acetoacetate
ethyl 2-chloroacetoacetate ethyl 2-methylacetoacetate
ethyl butyrylacetate.

The cyanoacetate reactants may be made by conventional methods. Various cyanoacetate esters such as methyl cyanoacetate and ethyl cyanoacetate are commercially available.

Illustrative cyanoacetate reactants for the compounds of the present invention include methyl cyanoacetate and ethyl cyanoacetate.

Suitable dialkyl chlorothiophosphates and dialkyl chlorophosphates which can be used as reactants include dimethyl chlorothiophosphate, diethyl chlorothiophosphate, dimethyl chlorophosphate, diethyl chlorophosphate, etc. Examples of suitable syntheses of dialkyl chlorothiophosphates and dialkyl chlorophosphates may be found in U.S. Pat. No. 2,715,136 and Steinberg, G. M., J. Org. Chem., 15, 637 (1950), respectively.

Any suitable conventional reaction conditions may be employed in the synthesis of the 4-hydroxy-2-trichloromethylpyrimidine compounds according to equations (A) and (C). See Henze et al., J. Org. Chem., 17, 1320 (1952); Falch et al., J. Med. Chem., 11, 608 (1968); U.S. Pat. No. 3,118,889; and Foeldi, et al., Chem. Berichte, 75, 755 (1942) as examples of such a synthesis.

A wide variety of conventional reaction conditions may be employed in the synthesis of the present compounds according to equations (B) and (D) and the present invention is not intended to be limited to any particular reaction conditions. For example, phosphorylation of the hydroxyl group of the 4-hydroxy-2-trichloromethylpyrimidine compound can be carried out by reacting the 4-hydroxy-2-trichloromethylpyrimidine compound with a selected dialkyl halothiophosphate or dialkyl halophosphate in the presence of a base such as triethylamine, pyridine, sodium carbonate, potassium carbonate, sodium ethoxide or sodium methoxide. Advantageously and preferably, the reactions are performed with at least an equimolar amount of dialkyl halothiophosphate or dialkyl halophosphate to the 4-hydroxy-2-trichloromethylpyrimidine compound, although a slight molar excess of the former may be used (e.g. from about 0.01 to about 1.0 mole excess). It is also preferred to use an equimolar amount of the base to the dialkyl halothiophosphate or dialkyl halophosphate. A solvent is not necessary, but any suitable inert solvent such as acetonitrile, diethyl ether, benzene or dimethylformamide may be employed.

Furthermore, the reaction temperature and time will both depend upon many factors including the exact reactants being employed. In most situations, reaction temperatures from about 35° C. to about 100° C. and reaction times from about 2 hours to about 48 hours are preferred.

The desired product may be recovered from the reaction mixture by any conventional means, for example, distillation, filtration, extraction, recrystallization, or the like. Finally, it should be noted that while the reactions illustrated by equations (A), (B), (C) and (D) are preferred, other synthetic methods for preparing compounds of the present invention may also be employed.

Representative compounds of the present invention include the following:

O-(6-methyl-2-trichloromethyl-4-pyrimidinyl)-O,O-dimethyl phosphorothionate
O-(6-methyl-2-trichloromethyl-4-pyrimidinyl)-O,O-diethyl phosphorothionate
O-(6-propyl-2-trichloromethyl-4-pyrimidinyl)-O,O-diethyl phosphorothionate
O-(6-amino-2-trichloromethyl-4-pyrimidinyl)-O,O-diethyl phosphorothionate
O-(5-chloro-6-methyl-2-trichloromethyl-4-pyrimidinyl)-O,O-diethyl phosphorothionate
O-(5,6-dimethyl-2-trichloromethyl-4-pyrimidinyl)-O,O-diethyl phosphorothionate
O-(6-methyl-5-nitro-2-trichloromethyl-4-pyrimidinyl)-O,O-diethyl phosphorothionate
O-(6-methyl-2-trichloromethyl-4-pyrimidinyl)-O,O-diethyl phosphoronate.

Also in accordance with the present invention, it has been found that the compounds of Formula (I) above may be utilized as effective insecticides. In practicing the method of the present invention, insects are contacted with an insecticidally effective amount of one or more of these compounds. It is to be understood that the term "insecticidally effective amount" as used in the specification and claims herein is intended to include any amount that will kill or control said insects when either employed by itself (i.e., in full concentration) or in a sufficient concentration within a carrier or other substance. Of course, this amount may be constantly changing because of the possible variations in many parameters. Some of these may include: the number and type of insects to be killed or controlled; the type of media to which the present compound can be applied (e.g. insect breeding grounds, crops); degree of effectiveness required; and type of carrier, if any. Generally speaking, applications of an aqueous spray containing at least about 5, more preferably in the range of about 30 to about 300, parts per million of the chemical of the present invention may give satisfactory insect control for most crops.

This step of contacting may be accomplished by applying this compound to the insects themselves, their eggs or larvae, their habitat, breeding grounds, dietary media, such as vegetation, crops and the like, and plant and animal life, including man, which these pests may attack. Preferably, it is advantageous to apply the chemicals of the present invention to the eggs of these insects. Also preferably, these chemicals can be applied to the insect larvae, the larvae habitat or the larvae dietary media. At the egg and larvae stages of the insects' cycle, the insect is usually relatively stationary and the insecticide normally can be applied in a more economical fashion with a greater expectation of good results.

The compounds of Formula (I) may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like. They may also be incorporated into baits upon which insects and their larvae feed.

The dusts are usually prepared by simply grinding together from about 1% to about 15% by weight of the active compound with a finely divided inert dileunt such as walnut flour, diatomaceous earth, fullers earth, attaclay, talc or kaolin. Dust concentrates are made in similar fashion except that about 16% to about 75% by weight of active compound is ground usually together with the diluent. In practice, dust concentrates are then generally admixed at the site of use with more inert diluent before it is applied to the plant foliage, soil or animals which are to be protected from insect attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray. For treatment of warm-blooded animals, this same spray-type application may be used or the wettable powder may be dispersed in the water of a dipping trough through which the animals are driven.

Emulsifiable liquids may be prepared by dissolving the active compound in an organic solvent, such as xylene or acetone, and admixing the thus formed solution with a surfactant or an emulsifier. The emulsifier liquid is then generally dispersed in water for spray or dip application.

It is also possible to formulate granulates whereby the active compound is dissolved in an organic solvent and the resulting solution is then applied to a granulated mineral or the like (e.g. bentonite, $SiO_2$ or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the active compound, or more than one active compound, of Formula (I) is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that the insecticide formulations, the ingredients which may make up such formulations other than the active compound, the dosages of these ingredients, and means of applying these formulations may include all known and conventional substances, amounts and means, respectively, that are suitable for obtaining the desired insecticidal result. And, therefore, such process parameters are not critical to the present invention.

Insecticides of the present invention may be effective for the control of broad classes of insects and their eggs and larvae. Specific illustrations of insects wherein insecticidal activity has been shown include Mexican bean beetle larvae, Southern armyworm larvae, and corn rootworm larvae.

The following examples further illustrate the present invention. All parts and percentages employed therein are by weight unless otherwise indicated. Yields given are percent molar yields.

EXAMPLE 1

Preparation of 4-Hydroxy-6-Methyl-2-Trichloromethylpyrimidine

A mixture of 44.4 g (0.28 mole) trichloroacetamidine, 32.0 g (0.28 mole) methyl acetoacetate, 37.5 g (0.28 mole) potassium carbonate, and 450 ml water was stirred for 3 days. A trace of solid was removed by filtration and the filtrate was made acidic with hydrochloric acid. The product precipitated out to give 28.9 g (46% yield; mp 173°–174° C.). The structure was confirmed via mp*, infrared and elemental analysis.

*J. Med. Chem., 11, 608 (1968)

Analysis for $C_6H_5N_2Cl_3O$

|  | C | H | N | Cl |
|---|---|---|---|---|
| Calculated: | 31.68 | 2.22 | 12.32 | 46.76 |
| Found: | 31.37 | 2.26 | 12.31 | 46.86 |

EXAMPLE 2

Preparation of O-(6-Methyl-2-Trichloromethyl-4-Pyrimidinyl)-O,O-Diethyl Phosphorothionate (a) A mixture of 4.5 g (0.02 mole) 4-hydroxy-6-methyl-2-trichloromethylpyrimidine, 2.1 g (0.02 mole) triethylamine and 3.8 g (0.02 mole) diethyl chlorothiophosphate was refluxed 10 hours. After stirring at room temperature for 16 hours longer, the mixture was filtered, and rotary evaporated to give 8.1 g of an oil. After several days, the oil was filtered to give 6.3 g (86% yield) of pure product. A small sample was distilled under vacuum (bp 138°–149° C. at 0.06 mm). The structure was confirmed via infrared, mass spectral, and elemental analysis.

Analysis for $C_{10}H_{14}N_2Cl_3SO_3P$

|  | C | H | N | Cl | S |
|---|---|---|---|---|---|
| Calculated: | 31.64 | 3.72 | 7.38 | 28.02 | 8.45 |
| Found: | 31.31 | 3.50 | 7.46 | 28.45 | 8.25 |

(b) A mixture of 4.6 g (0.02 mole) 4-hydroxy-6-methyl-2-trichloromethylpyrimidine, 5.7 g (0.03 mole) diethyl chlorothiophosphate, 2.8 g (0.03 mole) potassium carbonate, and 100 ml acetonitrile was refluxed 17 hours. On cooling, ether was added, the mixture was filtered, and solvent was stripped under rotary evaporation. A dark oil was isolated, 7.3 g (99%) product, assaying at over 96% via vapor phase chromatography, compared to the analytical sample prepared in (a).

EXAMPLE 3

Preparation of 5-Chloro-4-Hydroxy-6-Methyl-2-Trichloromethylpyrimidine

A mixture of 30.0 g (0.18 mole) trichloroacetamidine, 25.2 g (0.18 mole) potassium carbonate, 30.3 g (0.18 mole) ethyl-2-chloroacetoacetate, and 300 ml water was stirred 18 hours. The aqueous solution was decanted from heavier tars and acidified with hydrochloric acid. The precipitate that was formed, was filtered, washed, and dried to give 14.7 g (31% yield; mp 130°–145° C.) of crude product. An analytical sample recrystallized from cyclohexane had mp 156°–157° C. The structure was confirmed via infrared and elemental analysis.

Analysis for $C_6H_4N_2Cl_4O$

|  | C | H | N | Cl |
|---|---|---|---|---|
| Calculated: | 27.51 | 1.54 | 10.74 | 54.15 |
| Found: | 28.20 | 1.88 | 11.00 | 52.54 |

EXAMPLE 4

Preparation of
O-(5-Chloro-6-Methyl-2-Trichloromethyl-4-Pyrimidinyl)-O,O-Diethyl Phosphorothionate (a) A mixture of 5.3 g (0.02 mole) 5-chloro-4-hydroxy-6-methyl-2-trichloromethylpyrimidine, 2.2 g (0.02 mole) triethylamine, 4.0 g (0.02 mole) diethyl chlorothiophosphate and 25 ml ether was refluxed 18 hours. The mixture was filtered and the solvent rotary evaporated to give 5.9 g residue. This was chromatographed on silica gel to give 2.0 g (24%) oil (eluted with chloroform) that assayed at 95% product via vapor phase chromatography.

(b) A mixture of 5.3 g (0.02 mole) 5-chloro-4-hydroxy-6-methyl-2-trichloromethylpyrimidine, 2.1 g (0.02 mole) sodium carbonate, and 30 ml dimethylformamide was stirred 30 minutes. To this was added 3.8 g (0.02 mole) diethyl chlorothiophosphate and the mixture was heated at 65° C. for 3.75 hours. The reaction mixture was poured into water, extracted with ether, the ether extract washed with water, and dried over magnesium sulfate. Rotary evaporation yielded 3.8 g residue that was distilled under vacuum to give 1.5 g (18%) (bp 155° C. at 0.03 mm) of oil that assayed at 93% product via vapor phase chromatography.

The products from (a) and (b) were combined and the composite was distilled to give analytically pure product (97% assay via vapor phase chromatography (bp 160° C. at 0.1 mm).

The structure was confirmed via infrared and elemental analysis.

Analysis for $C_{10}H_{13}N_2Cl_4SO_3P$

|  | C | H | N | Cl | S |
|---|---|---|---|---|---|
| Calculated: | 29.00 | 3.16 | 6.77 | 34.25 | 7.74 |
| Found: | 28.90 | 3.15 | 7.00 | 34.61 | 7.68 |

EXAMPLE 5

Preparation of
6-Amino-4-Hydroxy-2-Trichloromethylpyrimidine

To a solution of 5.8 g (0.025 g atom) sodium in 150 ml methanol at 15° C. was added 11.5 g (0.1 mole) trichloroacetamidine. To this was added 11.5 g (0.1 mole) ethyl cyanoacetate in 100 ml methanol. The solution was refluxed 1 hour and then the solvent was removed under rotary evaporation to give a red paste. This was dissolved in 20 ml warm water and 100 ml of 50% aqueous acetic acid was added, causing product to precipitate. Filtration, washing, and drying of the product gave 16.1 g (71% yield; mp 225°-230° C. (decomposed). The structure was confirmed via infrared and elemental analysis.

Analysis for $C_5H_4N_3Cl_3O$

|  | C | H | N | Cl |
|---|---|---|---|---|
| Calculated: | 26.29 | 1.75 | 18.39 | 45.45 |
| Found: | 26.44 | 1.81 | 18.06 | 43.57 |

EXAMPLE 6

Preparation of
O-(6-Amino-2-Trichloromethyl-4-Pyrimidinyl)-O,O-Diethyl Phosphorothionate To 11.0 g (0.05 mole) 6-amino-4-hydroxy-2-trichloromethylpyrimidine in 100 ml ethanol was added a solution of 1.2 g (0.05 g atom) sodium in ethanol. This solution was stirred 30 minutes, filtered, and rotary evaporated to give 10.5 g gray powder. To 10.0 g (0.04 mole) of this powder slurried in 50 ml acetonitrile was added 7.5 g (0.04 mole) diethyl chlorothiophosphate and the mixture stirred 45 minutes. After filtration, the filtrate was rotary evaporated and the residue recrystallized from a mixture of ether/ligroin to give 4.5 g (24% yield) of product (mp 88°-89° C.). The structure was confirmed via infrared and elemental analysis.

Analysis for $C_9H_{13}N_3Cl_3SO_3P$

|  | C | H | N | Cl | S |
|---|---|---|---|---|---|
| Calculated: | 28.48 | 3.19 | 28.02 | 11.07 | 8.45 |
| Found: | 28.41 | 3.39 | 28.31 | 11.19 | 8.54 |

EXAMPLE 7

Preparation of
O-(6-Methyl-2-Trichloromethyl-4-Pyrimidinyl)-O,O-Dimethyl Phosphorothionate A mixture of 5.7 g (0.025 mole) 4-hydroxy-6-methyl-2-trichloromethylpyrimidine, 3.5 g (0.025 mole) potassium carbonate, and 50 ml benzene was azeotroped for 3 hours using a Dean Stark trap. To this was added 3.2 g (0.02 mole) dimethyl chlorothiophosphate, and the mixture refluxed 1 day. The reaction mixture was washed with 50 ml water, 5% aqueous potassium carbonate, and then water. Rotary evaporation of the benzene gave 4.8 g residue. The residue was distilled to yield, 2.9 g (41%) (bp 143° C. at 0.01-0.04 mm). An analytical sample was redistilled (bp 142° C. at 0.07 mm).

The structure was confirmed via infrared, elemental, and vapor phase chromatographic analysis.

Analysis for $C_8H_{10}N_2Cl_3SO_3P$

|  | C | H | N | Cl | S |
|---|---|---|---|---|---|
| Calculated: | 27.33 | 2.87 | 7.97 | 30.25 | 9.12 |
| Found: | 27.48 | 2.67 | 8.29 | 30.52 | 9.32 |

EXAMPLE 8

Preparation of
O-(6-Methyl-2-Trichloromethyl-4-Pyrimidinyl)-O,O-Diethyl Phosphoronate A mixture of 5.7 g (0.025 mole) 4-hydroxy-6-methyl-2-trichloromethylpyrimidine, 2.6 g (0.025 mole) triethylamine, 4.3 g (0.025 mole) diethyl chlorophosphate, and 75 ml chloroform was refluxed 21 hours. The solvent was then rotary evaporated, 100 ml of water added, and the mixture extracted with ether. The ether extract was rotary evaporated to give 2.7 g solid. This solid was washed with petroleum ether, and on concentration of the petroleum ether 1.1 g (12% yield) of oily product was isolated. The structure was confirmed via infrared and elemental analysis.

Analysis for $C_{10}H_{14}N_2Cl_3O_4P$

|  | C | H | N | Cl |
|---|---|---|---|---|
| Calculated: | 33.03 | 3.88 | 7.71 | 29.26 |
| Found: | 32.87 | 3.75 | 7.75 | 29.55 |

EXAMPLE 9

Preparation of 4-Hydroxy-6-Propyl-2-Trichloromethylpyrimidine

A mixture of 15.0 g (0.09 mole) trichloroacetamidine, 12.6 g (0.09 mole) potassium carbonate, 14.6 g (0.09 mole) ethyl butyrylacetate and 300 ml water was stirred overnight. The aqueous solution was decanted from the oil that formed and acidified with hydrochloric acid. The precipitate that formed was filtered, washed, and dried to give 2.6 g (11% yield). An analytical sample that was recrystallized from ligroin had mp 107°–110° C. The structure was confirmed via infrared and elemental analysis.

Analysis for $C_8H_9N_2Cl_3O$

|  | C | H | N | Cl |
|---|---|---|---|---|
| Calculated: | 37.60 | 3.55 | 10.97 | 41.63 |
| Found: | 37.34 | 3.59 | 10.78 | 41.45 |

EXAMPLE 10

Preparation of O-(6-Propyl-2-Trichloromethyl-4-Pyrimidinyl)-O,O-Diethyl Phosphorothionate A mixture of 5.1 g (0.02 mole) 4-hydroxy-6-propyl-2-trichloromethylpyrimidine, 2.1 g (0.02 mole) triethylamine, 3.8 g (0.02 mole) diethyl chlorothiophosphate, and 100 ml ether was refluxed 29 hours. The solution was washed with water, 5% aqueous potassium carbonate, and then water. Rotary evaporation of the solvent gave 5.4 g residue. The residue was taken up in petroleum ether, filtered, and rotary evaporated. Distillation yielded 1.0 g (13% yield) of product (bp 159° C. at 0.07–0.017 mm).

The structure was confirmed via infrared, elemental, and vapor phase chromatographic analysis.

Analysis for $C_{12}H_{18}N_2Cl_3SO_3P$

|  | C | H | N | Cl | S |
|---|---|---|---|---|---|
| Calculated: | 35.35 | 4.45 | 6.87 | 26.09 | 7.87 |
| Found: | 35.27 | 4.44 | 6.66 | 26.17 | 8.08 |

Formulations

Aqueous dispersions of a test chemical are most easily utilized for general screening. To prepare such a dispersion, the chemical is dissolved in a solution of acetone containing 500 ppm of a nonionic surfactant, e.g., TRITON X-155[1]. The resulting solution is diluted with water (1:9) to obtain a mixture of 10% acetone, 50 ppm surfactant, the desired weight percent of test candidate, and the remaining balance as water. If further dilutions are required, water is added to this stock solution and the surfactant maintained at 50 ppm.

[1] Manufactured by Rohm and Haas of Philadelphia, Pa. and is a polyether alcohol.

Rating System

All tests use a scale of 0 to 10 with 0 representing no control and 10 representing full control.

Mexican Bean Beetle

Leaves of young bean plants are removed from the plants by cutting the petioles and are dipped into the test chemical at 260 ppm for the primary test. These are placed in a water reservoir to maintain leaf turgidity and, after the chemical deposit is dry, ten 4-day old larvae of the Mexican bean beetle are placed on them. After 5 days, observations are made on mortality and feeding inhibition. Any effects on metamorphosis are noted. In secondary testing, the same procedure is followed, except lower concentrations of the test chemical are employed. See Table I for the results of these tests.

TABLE I

| Insecticidal Activity Against Mexican Bean Beetle | | | | | | | |
|---|---|---|---|---|---|---|---|
| | | Rate | | | | | |
| Compound | Effect | 260 ppm | 130 ppm | 65 ppm | 33 ppm | 16 ppm | 8 ppm |
| Example 2 | Kill | 7 | | | | | |
| | Feed Inhibition | 8 | | | | | |
| Example 6 | Kill | 10 | 10 | 10 | 8.5 | 1 | 1.5 |
| | Feed Inhibition | 9 | 8.5 | 7.5 | 3.5 | 3.5 | 4.5 |
| Example 8 | Kill | | | 10 | 10 | 10 | 2 | 5 |
| | Feed Inhibition | | | 10 | 10 | 10 | 1 | 6 |

Southern Armyworm

This test is performed as above except that 1-day old larvae of the southern armyworm are used. The test chemical is used at concentrations of 130 ppm and lower. See Table II for the results of these tests.

TABLE II

| Insecticidal Activity Against Southern Armyworm | | | | | | | |
|---|---|---|---|---|---|---|---|
| | | Rate | | | | | | |
| Compound | Effect | 130 ppm | 65 ppm | 33 ppm | 16 ppm | 8 ppm | 4 ppm | 2 ppm |
| Example 2 | Kill | | | 10 | 10 | 10 | 2.5 | 0 |
| | Feed Inhibition | | | 10 | 10 | 9 | 5 | 2 |
| Example 6 | Kill | 6.5 | 3.5 | 6 | | | | |
| | Feed Inhibition | 8 | 4 | 4.5 | | | | |
| Example 7 | Kill | | 10 | 10 | 10 | 1 | | |
| | Feed Inhibition | | 10 | 10 | 10 | 3 | | |
| Example 8 | Kill | 6 | 0 | 0 | | | | |
| | Feed Inhibition | 8 | 6 | 2 | | | | |

Corn Rootworm

For the primary test, the compound is mixed at 10 lb/acre with soil and held for 3 days in a sealed cup. The cover is removed and two corn seedlings are placed in the cup. Ten southern corn rootworm larvae are added to the soil surface, the cover is replaced, and the containers incubated at 75° F. After 4 days, the soil is sifted and observations made on mortality and feed inhibition. In secondary testing, the same procedure is followed, except lower concentrations of the test chemical are employed. See Table III for the results of these tests.

TABLE III

Insecticidal Activity Against Corn Rootworm

| Compound | Effect | 10 lb/acre | 5 lb/acre | 2.5 lb/acre | 1.25 lb/acre |
|---|---|---|---|---|---|
| Example 2 | Kill | 10 | 10 | 1.5 | 1.5 |
| | Feed Inhibition | 9 | 8.5 | 3.5 | 5 |
| Example 6 | Kill | 4 | | | |
| | Feed Inhibition | 5 | | | |

Bean Aphid

This test is performed on the adult black bean aphid feeding on nasturtium plants. For the primary test, the foliage and the aphids are sprayed with the test candidate at 260 ppm and the soil is drenched at 25 lb/acre. After 1 and 5 days, the dead aphids, which have fallen onto a paper collar, are counted along with any living aphids and a rating obtained. Secondary tests are performed at lower concentrations using a spray application. See Table IV for the results of these tests.

TABLE IV

Insecticidal Activity Against Bean Aphid

| Compound | Effect | 130 ppm | 65 ppm | 33 ppm | 16 ppm | 8 ppm |
|---|---|---|---|---|---|---|
| Example 7 | Kill | 10 | 10 | 10 | 10 | 0 |
| Example 8 | Kill | 10 | 10 | 10 | 10 | 10 |

What is claimed is:

1. A compound having the formula:

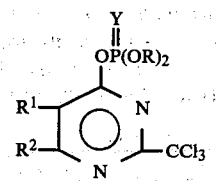

wherein Y is an atom selected from the group consisting of sulfur and oxygen; R is a lower alkyl group having 1 to 4 carbon atoms; $R^1$ is hydrogen, a lower alkyl group having 1 to 4 carbon atoms, halo or nitro; and $R^2$ is a lower alkyl group having 1 to 4 carbon atoms or an amino group.

2. The compound of claim 1 wherein Y is sulfur.
3. The compound of claim 2 wherein $R^1$ is hydrogen.
4. The compound of claim 3 wherein $R^2$ is a lower alkyl group having 1 to 4 carbon atoms.
5. The compound of claim 3 wherein $R^2$ is an amino group.
6. The compound of claim 2 wherein $R^1$ is halo.
7. The compound of claim 6 wherein $R^2$ is a lower alkyl group having 1 to 4 carbon atoms.
8. The compound of claim 6 wherein $R^2$ is an amino group.
9. The compound of claim 1 wherein Y is oxygen.
10. The compound of claim 9 wherein $R^1$ is hydrogen.
11. The compound of claim 9 wherein $R^2$ is a lower alkyl group having 1 to 4 carbon atoms.
12. A method of controlling insects which comprises contacting said insects with an insecticidally effective amount of a compound having the formula:

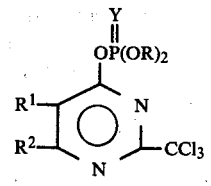

wherein Y is an atom selected from the group consisting of sulfur and oxygen; R is a lower alkyl group having 1 to 4 carbon atoms; $R^1$ is hydrogen, a lower alkyl group having 1 to 4 carbon atoms, halo or nitro; and $R^2$ is a lower alkyl group having 1 to 4 carbon atoms or an amino group.

13. The method of claim 12 wherein Y is sulfur.
14. The method of claim 13 wherein $R^1$ is hydrogen.
15. The method of claim 14 wherein $R^2$ is a lower alkyl group having 1 to 4 carbon atoms.
16. The method of claim 15 wherein said compound is O-(6-methyl-2-trichloromethyl-4-pyrimidinyl)-O,O-diethyl phosphorothionate.
17. The method of claim 15 wherein said compound is O-(6-methyl-2-trichloromethyl-4-pyrimidinyl)-O,O-dimethyl phosphorothionate.
18. The method of claim 14 wherein $R^2$ is an amino group.
19. The method of claim 18 wherein said compound is O-(6-amino-2-trichloromethyl-4-pyrimidinyl)-O,O-diethyl phosphorothionate.
20. The method of claim 12 wherein said compound is O-(6-methyl-2-trichloromethyl-4-pyrimidinyl)-O,O-diethyl phosphoronate.

* * * * *